United States Patent [19]

Chu

[11] Patent Number: 4,560,818

[45] Date of Patent: Dec. 24, 1985

[54] PROCESS FOR THE OXIDATIVE DEHYDROGENATION OF ETHYLTOLUENE TO METHYLSTYRENE

[75] Inventor: Chin-Chiun Chu, North Brunswick, N.J.

[73] Assignee: Mobil Oil Corporation, New York, N.Y.

[21] Appl. No.: 685,584

[22] Filed: Dec. 24, 1984

[51] Int. Cl.[4] .................................................. C07C 4/12
[52] U.S. Cl. ....................... 585/443; 585/440; 585/442; 585/444
[58] Field of Search ................ 585/443, 442, 440, 444

[56] References Cited

U.S. PATENT DOCUMENTS

| | | | |
|---|---|---|---|
| 3,247,278 | 4/1966 | Garwood et al. | 208/46 |
| 3,403,192 | 9/1968 | Vadekar et al. | 585/443 |
| 3,607,966 | 9/1971 | Croce | 585/443 |
| 3,855,330 | 12/1974 | Mendelsohn et al. | 585/443 |
| 3,957,897 | 5/1976 | Vrieland et al. | 585/443 |
| 3,998,760 | 12/1976 | Christmann et al. | 585/443 |
| 4,002,696 | 1/1977 | Hoppstock | 585/443 |
| 4,020,120 | 4/1977 | Christmann et al. | 585/443 |
| 4,086,287 | 4/1978 | Kaeding et al. | 585/466 |
| 4,400,568 | 8/1983 | Hofmann et al. | 585/443 |

FOREIGN PATENT DOCUMENTS 1155527  6/1969  United Kingdom .

*Primary Examiner*—D. E. Gantz
*Assistant Examiner*—Helane Myers
*Attorney, Agent, or Firm*—Alexander J. McKillop; Michael G. Gilman; Edward J. Trojnar

[57] ABSTRACT

Ethyltoluene is oxidatively dehydrogenated to methylstyrene selectivity and in high conversions by treatment with hydrogen sulfide and oxygen at elevated temperatures of about 450° C. to 700° C. over magnesium oxide catalyst.

6 Claims, No Drawings

PROCESS FOR THE OXIDATIVE DEHYDROGENATION OF ETHYLTOLUENE TO METHYLSTYRENE

BACKGROUND OF THE INVENTION

1. Field of the Invention

This invention is concerned with the oxidative dehydrogenation of ethyltoluenes to the corresponding methylstyrenes.

2. Description of the Prior Art

Various processes have been proposed for the oxidative dehydrogenation of organic compounds to the corresponding unsaturated compounds. U.S. Pat. No. 3,403,192, which is incorporated herein by reference, discloses a vapor phase oxidative dehydrogenation process using oxygen and hydrogen sulfide in contact with a metal, metal oxide, or a metal hydroxide catalyst, usually with a promoter. Good conversions of ethylbenzene to styrene were achieved in the patented process, for example, but the dehydrogenation of ethyltoluene to methylstyrene often poses additional problems because of the vulnerability of the methyl group in the ethyltoluene to decomposition. Indeed, many prior art catalysts and processes which are entirely suitable for use in the dehydrogenation of ethylbenzene are found to result in poor conversion and selectivity when applied to the dehydrogenation of ethyltoluene.

SUMMARY OF THE INVENTION

The process of this invention comprises the oxidative dehydrogenation of an ethyltoluene by contacting ethyltoluene in the vapor phase with hydrogen sulfide, oxygen and magnesium oxide catalyst.

DETAILED DESCRIPTION OF THE INVENTION

The process of the present invention is useful for making monomers which, in turn, can be used to prepare valuable polymers and other resinous compositions such as polyesters.

In addition to the ethyltoluene feed, hydrogen sulfide and oxygen are used in the process. The oxygen can be used as pure oxygen or as an oxygen-containing gas such as air, mixtures of air and nitrogen, and mixtures of oxygen and nitrogen. The molar ratio of $H_2S:O_2$: feed is generally between 1.1:0.6:1 and 1.5:3:1.

The ethyltoluene feeds useful in this invention are isomeric mixtures of the isomers which can have various proportions of the isomers, and generally comprise the meta- and para-isomers in which the para-isomer constitutes 30 to 99 percent of the isomers.

The process of this invention is advantageously used for the dehydrogenation of para-ethyltoluene feeds produced in accordance with U.S. Pat. No. 4,086,287, which is incorporated herein by reference in its entirety. The feeds described in the patent are ethyltoluene mixtures which are high in para content, e.g. 90 percent or more and preferably 95 percent or more; and a very low ortho-isomer content, e.g., less than 0.1 percent; the remainder being the meta-isomer. The corresponding monomers which are prepared by dehydrogenation of the para-ethyltoluenes to para-methylstyrenes have particularly advantageous properties when they are polymerized, or when copolymerized with other monomers.

The temperature of the reaction, i.e., the temperature of the catalyst bed, is preferably between about 450° C. and 700° C., and most preferably between about 500° C. and 650° C.

The catalyst used in the process of this invention is magnesium oxide.

The process of this invention is advantageously carried out in a continuous manner. Accordingly, any apparatus suitable for continuous reacting can be used. The reactor can be equipped with a suitable preheater section. For example, when operating with a 600° C. catalyst bed temperature a preheat temperature of about 600° to 680° C. may be used. The use of steam is not necessary and the costs attendant to its use are eliminated.

The following non-limiting examples are illustrative of the process of this invention.

EXAMPLE

To a reactor containing 10 cc (12.2 g) MgO ⅛" extrudate heated at 600° C. was passed through 4.4 ml/hr p-ethyltoluene and 14.3 cc/min hydrogen sulfide together with various amount of air. The results are as follows.

| | | | | | |
|---|---|---|---|---|---|
| p-Ethyltoluene (mole ratio) | 1 | 1 | 1 | 1 | 1 |
| $H_2S$ (mole ratio) | 1.13 | 1.13 | 1.13 | 1.13 | 1.13 |
| Oxygen (in Air) (mole ratio) | 0 | .57 | 1.1 | 1.8 | 2.5 |
| % Conversion p-ethyltoluene | 33 | 41 | 48.5 | 64.4 | 73.9 |
| % Selectivity p-methylstyrene | 75 | 80.3 | 86 | 89.3 | 90.9 |

The presence of both $H_2S$ and $O_2$ gave 73.9% p-ethyltoluene conversion and 90.9% selectivity to p-methylstyrene.

Conventional steam dehydrogenation of p-ethyltoluene gave about 65% conversion and 91–92% p-methylstrene selectivity at 620° C. At the comparable temperature at 600° C. conversions were about 40%.

Although the present invention has been described with preferred embodiments, it is to be understood that modifications and variations may be restored to, without departing from the spirit and scope of this invention, as those skilled in the art will readily understand. Such variations and modifications are considered to be within the purview and scope of the appended claims.

I claim:

1. A process for the oxidative dehydrogenation of p-ethyltoluene to form p-methylstyrene in a selectivity of at least 86%, comprising contacting p-ethyltoluene with oxygen and hydrogen sulfide in the presence of magnesium oxide catalyst, at an elevated temperature; in which the molar ratio of oxygen to hydrogen sulfide is 1.6:1 or greater, and the molar ratio of hydrogen sulfide to p-ethyltoluene is 1.1:1 to 1.5:1.

2. The process of claim 1 which is conducted at a temperature of about 450° C. to 700° C.

3. The process of claim 1 in which is conducted at a temperature of 500° C. to 650° C.

4. The process of claim 2 in which the molar ratio of oxygen to hydrogen sulfide is 1.6:1 to 3:1.

5. The process of claim 1 in which the molar ratio of oxygen to hydrogen sulfide is 1.6:1 to 3:1.

6. The process of claim 3 in which the molar ratio of oxygen to hydrogen sulfide is 1:1 to 3:1.

* * * * *